(12) United States Patent
Kaizuka

(10) Patent No.: US 7,104,948 B2
(45) Date of Patent: Sep. 12, 2006

(54) BRACELET THAT RADIATES ANION AND FAR INFRARED RAYS

(75) Inventor: Kazutoshi Kaizuka, Fukuoka (JP)

(73) Assignee: Create Co., Ltd., Fukuoka (JP)

( * ) Notice: Subject to any disclaimer, the term of this patent is extended or adjusted under 35 U.S.C. 154(b) by 491 days.

(21) Appl. No.: 10/680,011

(22) Filed: Oct. 6, 2003

(65) Prior Publication Data

US 2005/0075530 A1 Apr. 7, 2005

(51) Int. Cl.
*A61N 1/00* (2006.01)

(52) U.S. Cl. ............................................. 600/15
(58) Field of Classification Search ............... 600/9–15
See application file for complete search history.

(56) References Cited

U.S. PATENT DOCUMENTS

| 236,522 | A | 1/1881 | Wilson |
|---|---|---|---|
| 278,944 | A | 6/1883 | Hauce |
| 294,309 | A | 2/1884 | Campbell |
| 1,455,696 | A | 5/1923 | Wright |

(Continued)

FOREIGN PATENT DOCUMENTS

| DE | 3120576 A1 | 1/1983 |
|---|---|---|
| DE | 19711676 A1 | 9/1998 |
| DE | 19803175 A1 | 7/1999 |
| EP | 0 077600 A2 | 4/1983 |
| EP | 0 0160320 A2 | 11/1985 |
| EP | 1 086634 A1 | 3/2001 |
| GB | 1210385 | 10/1970 |
| GB | 2301772 A | 12/1996 |
| GB | 0927544 B1 | 7/1999 |
| JP | 63150011 | 6/1988 |
| JP | 63238808 | 10/1988 |
| JP | 03241025 | 10/1991 |
| JP | 03250088 | 11/1991 |
| JP | 956472 | 3/1997 |
| JP | 09121996 | 5/1997 |
| JP | 11056425 | 3/1999 |
| JP | 2000-128750 | 5/2000 |
| JP | 2001288679 | 10/2001 |
| JP | 2002-313855 | 10/2002 |
| KR | 0117366 | 7/1996 |
| RU | 2108299 | 4/1998 |
| WO | WO 02/058449 A2 | 8/2002 |
| WO | WO 02/058449 A3 | 8/2002 |

OTHER PUBLICATIONS

Sakamoto, et al., Effect of a Toothbrush with Ion–coated Nylon Filaments on Gingival Tissue in Dogs and Dental Plaque Accmulation in a Man, 2002, pp. 221–228, J. Dent. Hlth. 52; Okayama Univ. School of Medicine, Japan.
Watanabe, et al., A Clinical Study to Evaluate the Effectiveness of a Multi–mineral Nylon Abrasive Filament (NAF) Toothbrush; pp. 1–12, Okayama University School of Medicine, Japan.

*Primary Examiner*—John P. Lacyk
(74) *Attorney, Agent, or Firm*—Squire, Sanders & Dempsey, LLP

(57) ABSTRACT

The present invention is related to a bracelet irradiating anion and far infrared rays, comprising metal where anion-radiating material layer and gold plate layer are sequentially coated on the surface of a "C" shape core (10) with a connecting arm (20) and a clasp assembly including magnetic coupling clasps. This bracelet looks very elegant because of the gold plate on the exterior of the bracelet, and static electricity occurs due to the friction between the bracelet and the human hand, and it can irradiate anion and far infrared rays more effectively through sunlight, and by supplying the far infrared rays to the skin, the ion balance of the cell can be controlled, and it can change the electric potential of the skin to normal value, and can promote blood circulation and metabolism, complex biorhythm, and body cell is activated and blood pressure is lowered, increasing the tissue regeneration capacity, preventing the aging phenomena.

8 Claims, 7 Drawing Sheets

U.S. PATENT DOCUMENTS

| | | | |
|---|---|---|---|
| 2,155,282 A | 4/1939 | Schoenling | |
| 3,228,845 A | 1/1966 | Nagjar | |
| 3,613,143 A | 10/1971 | Muhler et al. | |
| 3,618,154 A | 11/1971 | Muhler et al. | |
| 3,703,766 A | 11/1972 | Tibbals | |
| 4,035,865 A | 7/1977 | McRae et al. | |
| 4,095,587 A * | 6/1978 | Ishikawa | 600/15 |
| 4,143,126 A | 3/1979 | Gaffar | |
| 4,151,850 A | 5/1979 | Nathe et al. | |
| D253,973 S | 1/1980 | Rosse | |
| 4,231,137 A * | 11/1980 | Fujimoto | 24/303 |
| 4,242,567 A | 12/1980 | Carter | |
| 4,477,716 A | 10/1984 | Thaler et al. | |
| 4,500,939 A | 2/1985 | Gueret | |
| 4,549,560 A | 10/1985 | Andis | |
| 4,567,904 A | 2/1986 | Pitcher et al. | |
| 4,610,925 A | 9/1986 | Bond | |
| 4,739,151 A | 4/1988 | Smal | |
| 4,740,669 A | 4/1988 | Takimae | |
| 4,886,972 A | 12/1989 | Nakai et al. | |
| 4,917,078 A | 4/1990 | Zaborowski | |
| D309,354 S | 7/1990 | Rizzuto et al. | |
| 5,056,227 A | 10/1991 | Kramer | |
| 5,124,143 A | 6/1992 | Muhlemann et al. | |
| 5,224,397 A | 7/1993 | Yoo | |
| 5,226,020 A * | 7/1993 | Li et al. | 368/10 |
| 5,266,304 A | 11/1993 | Baffelli et al. | |
| 5,357,988 A | 10/1994 | Nakamura | |
| 5,531,675 A | 7/1996 | Yoo | |
| 5,787,525 A | 8/1998 | Sugihara et al. | |
| 5,799,671 A | 9/1998 | Takimae | |
| 5,848,599 A | 12/1998 | Todd | |
| 5,891,473 A | 4/1999 | Stanier | |
| D411,333 S | 6/1999 | Smal | |
| 5,934,293 A | 8/1999 | Kaizuka | |
| 5,935,483 A | 8/1999 | Kong | |
| 5,987,688 A | 11/1999 | Roberts et al. | |
| 6,029,277 A | 2/2000 | Picchione, II | |
| 6,029,356 A | 2/2000 | Sprinkle | |
| D424,742 S | 5/2000 | Hirata | |
| 6,105,261 A | 8/2000 | Ecer | |
| 6,205,674 B1 | 3/2001 | Kaizuka | |
| 6,432,036 B1 * | 8/2002 | Kim | 600/9 |
| 6,506,267 B1 * | 1/2003 | Fujiyasu et al. | 148/430 |
| 6,516,229 B1 * | 2/2003 | Wey | 607/100 |

\* cited by examiner

BRACELET THAT RADIATES ANION AND FAR INFRARED RAYS

BACKGROUND OF THE INVENTION

1. Field of the Invention

The present invention is directed to a bracelet that radiates anion and far infrared rays, those use of which purifies blood, activates body cells, increases immunity, stabilizes nerves, enhances respiratory and internal organs, reduces fatigue, assists in maintaining health and promoting the activation of body cells.

2. General Background and State of the Art

As health issues get more attention, a substantial number of health-related products are being released in the market such as for example a product that cures shoulder problems by facilitating the blood circulation with magnetic energy or far infrared rays.

As another example, Japanese Patent Publication SHO 10-295830 discloses an adhesive, for adjusting bodily ions, installed in between a metal with a positive charge on the one side and a negative charge on the other side. This adhesive is claimed to generate ions effectively, provide electric stimulus to the spots on the body suitable for acupuncture by the effect of minus ions and local fine current; to transfer to the autonomic nerve through neurons; to promote the body function of the sympathetic nerve or parasympathetic nerve, and to increase the blood flow by enlarging the capillary vessels of the diseased or ailing body part.

However, this adhesive has the drawback that it is hard to get an effective potential difference between the positive and negative electric potential, and the ion generation function is not sufficient. In addition, the effect is limited to the spot where it is applied, and if wider treatment on an area is needed, a larger sized adhesive is required, making the movement of the body difficult.

Accordingly, to allow the body to move freely yet maintain ion generation devices in contact with the skin, various accessories are being developed such as bracelets, necklaces, and rings in order to enhance health by supplying ions to the surface of the body.

Korean Patent Publication No. 96-28107 reveals a bracelet on which a magnet is installed to control biorhythm by balancing anion and cation that flows in the human body. Likewise, Korean Utility Model Publication No. 95-24281 discloses a ceramic bracelet radiating far infrared rays where the ceramic is installed on the back side of the bracelet. But magnets or ceramics that radiate infrared rays often became detached from the bracelet, and the effect on the body was not satisfactory.

INVENTION SUMMARY

The objective of the present invention is to address the limitations of the previous products, and provide an elegant, comfortable, and cure-effective bracelet that radiates anion and far infrared rays, by radiating far infrared rays and anion to the human body.

The embodiment of the bracelet that irradiates anion and far infrared rays, according to the invention, comprises a metal core with an anion-radiating material layer and a gold plate layer sequentially coated on the metal core configured in a "C" shape main part and a connecting arm and clasp whose ends are linked to both ends of the main part by hinge pins so that the bracelet can be engaged or disengaged with a magnet attached to the clasp of the connecting arm.

About 60 to 70% of the human body is composed of bodily fluid containing electrolytes and non-electrolytes. Electrolytes are composed of the balanced cations and anions, and if this balance is lost, human body is vulnerable to various illnesses.

It is known that such difference in the distribution of ions enclosing human cells is significantly related to the nerve cells, and has significant influence on the recovery of health or deterioration of disease.

These cations and anions exist by using cellular walls as barriers, the cellular wall permeability differing in accordance with the amount of positive, negative, and dipolar electric potentials. Ions move around the human body according to a certain rule, influenced by the strength or distribution of energy in the inside and outside environment.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood with reference to the following figures. The components in the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

The following is the description of the preferred embodiment, where the attached figures will be also explained.

Figure 1:
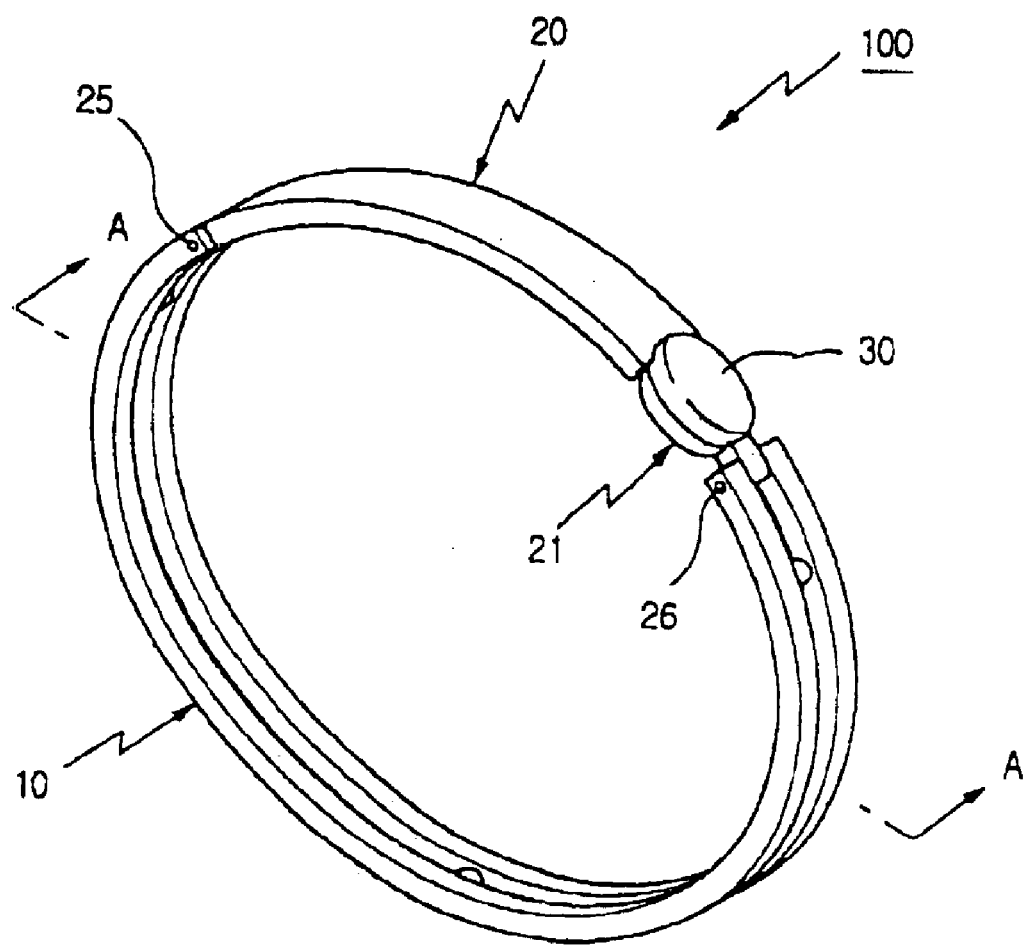
FIG. 1 is a perspective view illustrating the whole appearance of the bracelet that radiates anion and far infrared rays.

FIG. 1 is a perspective view illustrating the whole appearance of the bracelet that radiates anion and far infrared rays.

The bracelet (100), in accordance with the present invention that radiates anion and far infrared rays, is composed of "C" shaped main part (10) and a connecting arm (20).

The main part (10) of the bracelet (100), in accordance with the present invention, is designed to radiate anion and far infrared rays. The main part (10) is C-shaped, and is connected to a connecting arm (20) with a clasp (21) with one end connected to hinge pin (25) so that the connecting arm (20) can rotate the main part (10) about an axle or pin (25). The other end of the main part (10) has a pin (26) connected to a clasp (30) which couples to clasp (21) to allow the bracelet (100), in accordance with the present invention, to be opened and closed.

Figure 4A:
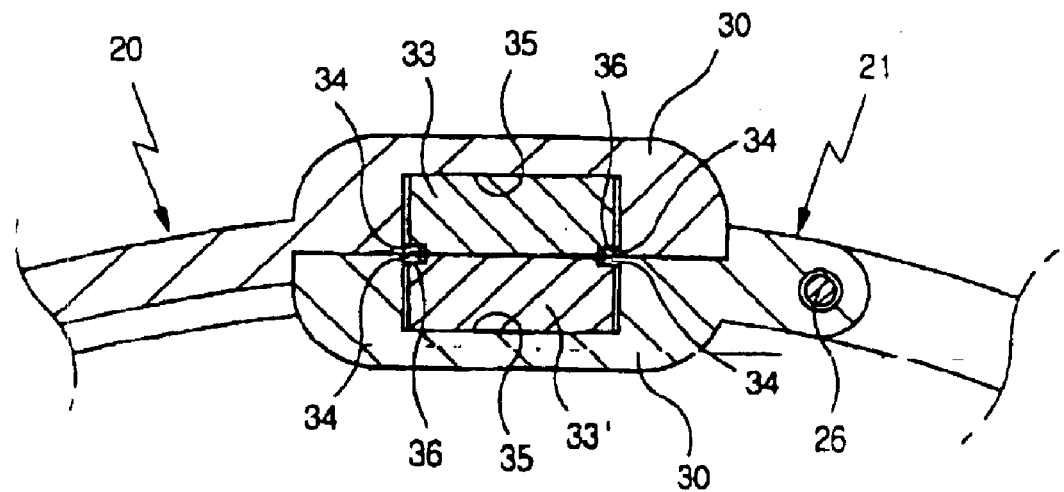
FIG. 4a is a schematic enlarged cross-section illustrating the closed connector of the bracelet that radiates anion and far infrared rays.
Figure 4B:
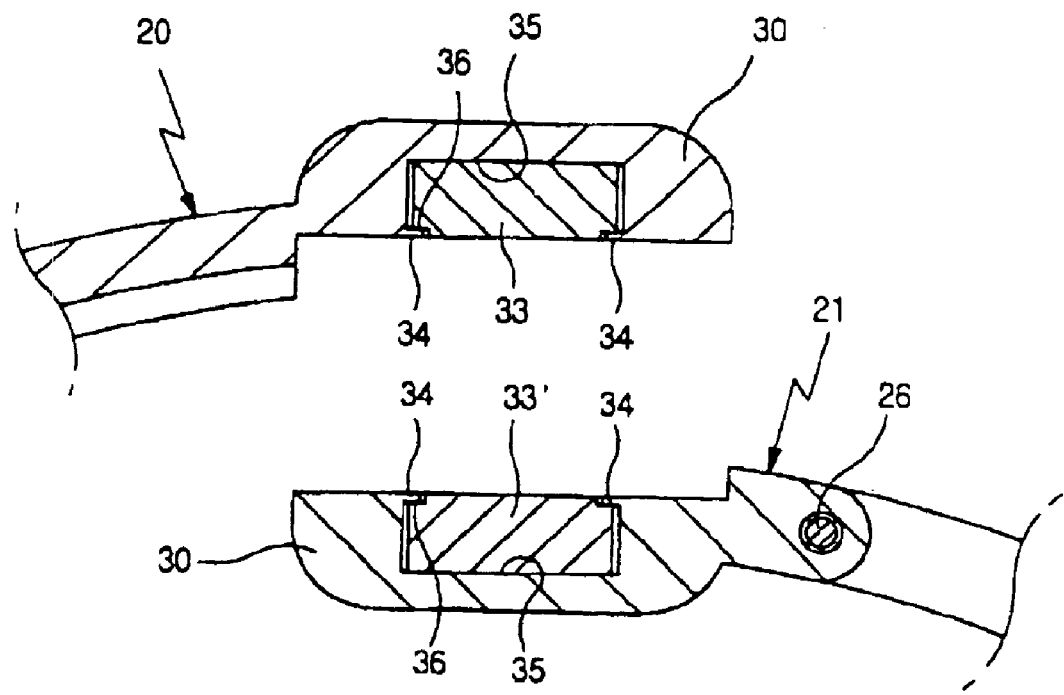
FIG. 4b is a schematic enlarged cross-section illustrating the unlocked connector of the bracelet that radiates anion and far infrared rays.
Figure 5:
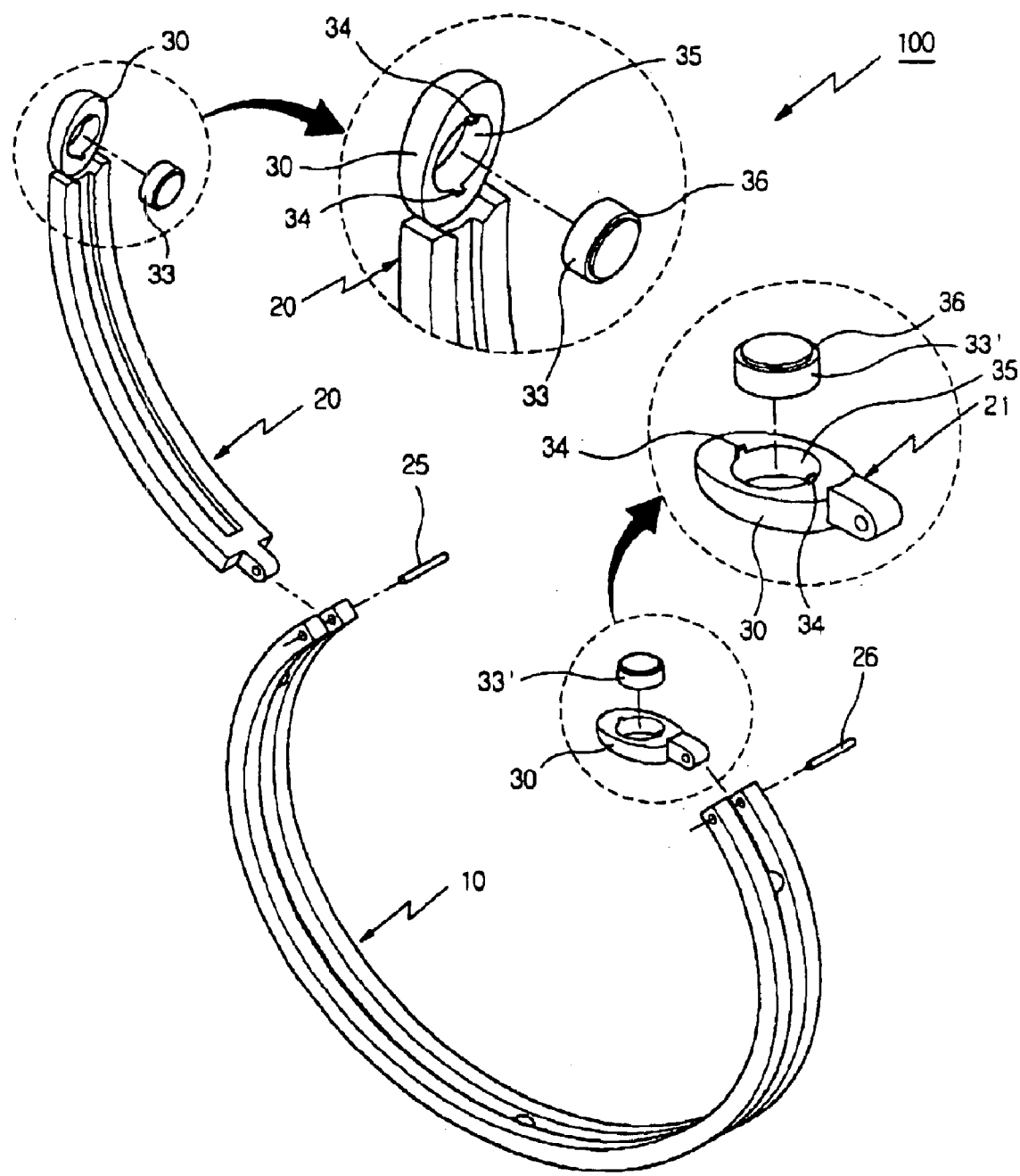
FIG. 5 is a perspective view illustrating the disassembled bracelet that radiates anion and far infrared rays.

The connecting arm (20) has the clasp (21) as shown in FIGS. 4a, 4b, 5. The clasp (21) defines a space (35) where magnet (33) is installed in a fixing part that holds the magnet (33).

It is desirable to have a projection (36) around the magnet (33) so that when the magnet (33) couples with the magnet (33') of the clasp (30) the projection (36) mates with the space (35) of the connector (30), and can be afixed easily. The magnets (33, 33') are held in place by fixing parts (34). Alternatively, one of the magnets (33, 33') could be a ferromagnetic material.

The magnets (33, 33') installed in the clasps (30, 21) not only hold the connecting arm (20) in place but they also help circulate the blood due to the influence of the magnetic field when wearing the bracelet (100) in accordance with the present invention which also radiates anion and far infrared rays.

Figure 2:
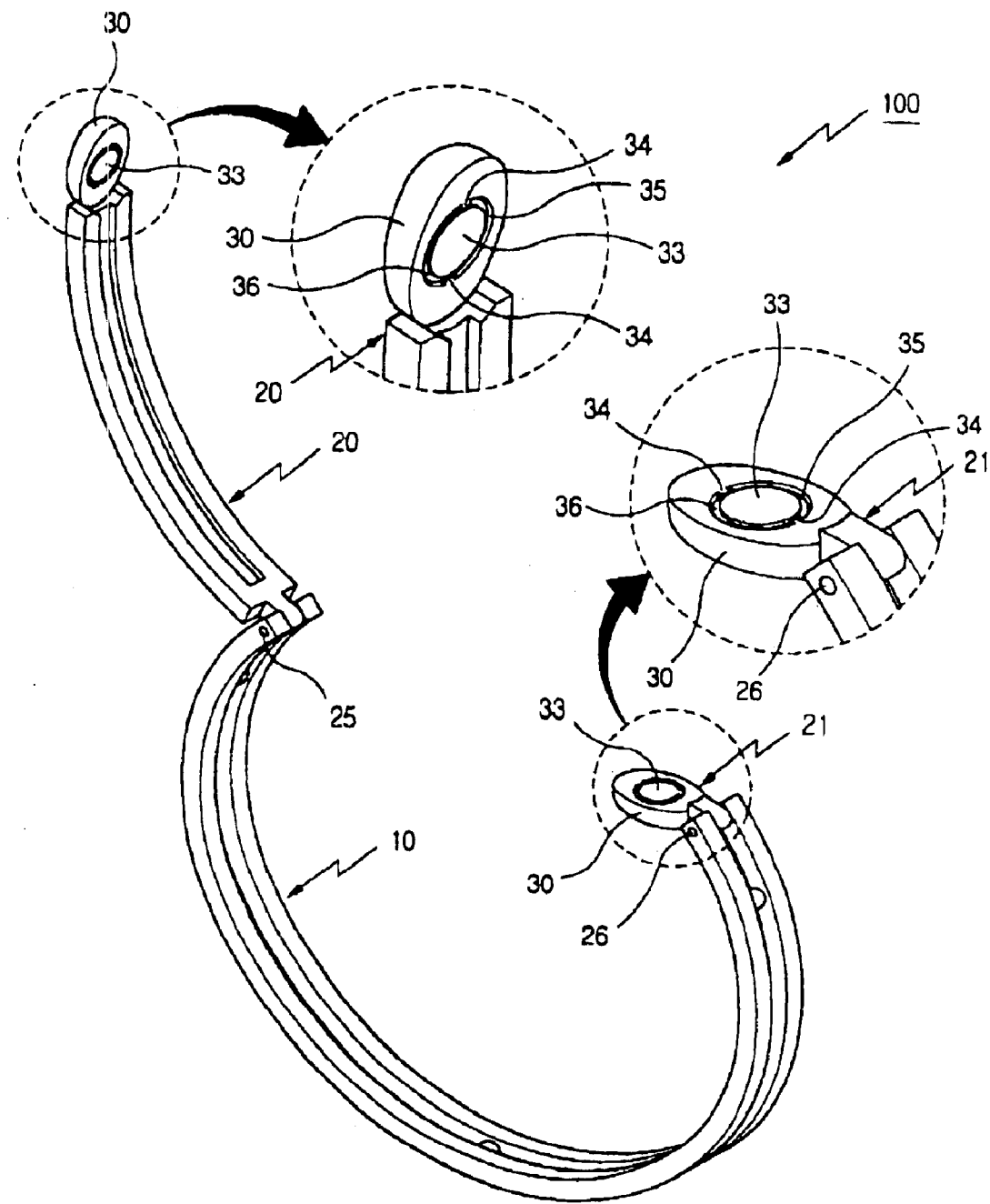
FIG. 2 is a perspective view illustrating how to use the bracelet that radiates anion and far infrared rays.
Figure 3:
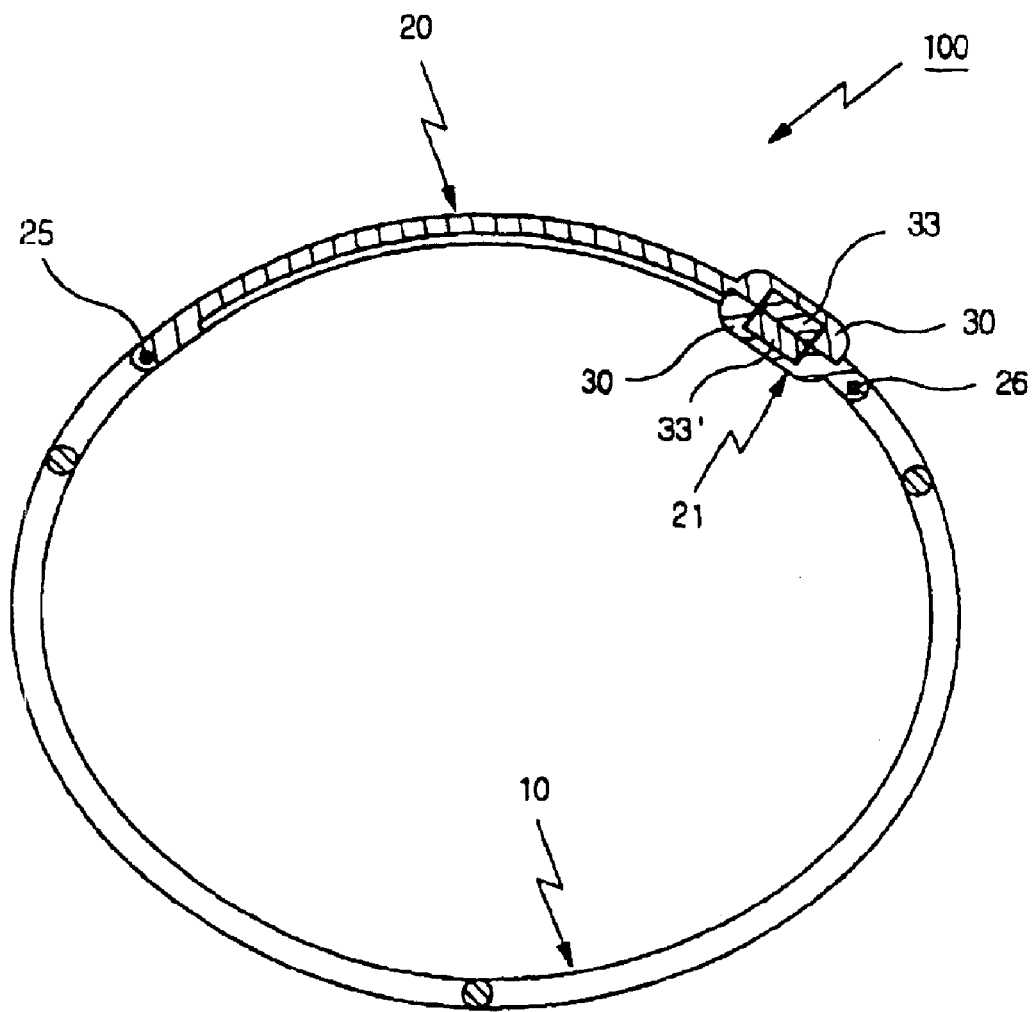
FIG. 3 is a schematic cross-sectional view along the line A—A of FIG. 1.

When using the bracelet (100) as shown in FIG. 2, a user pulls up the connecting arm (20) to disengage the magnet (33) of the clasp (30), and open the bracelet, by separating the magnet (33) installed in the end of connecting arm (20) from the magnet (33') of the clasp (21).

Figure 6:
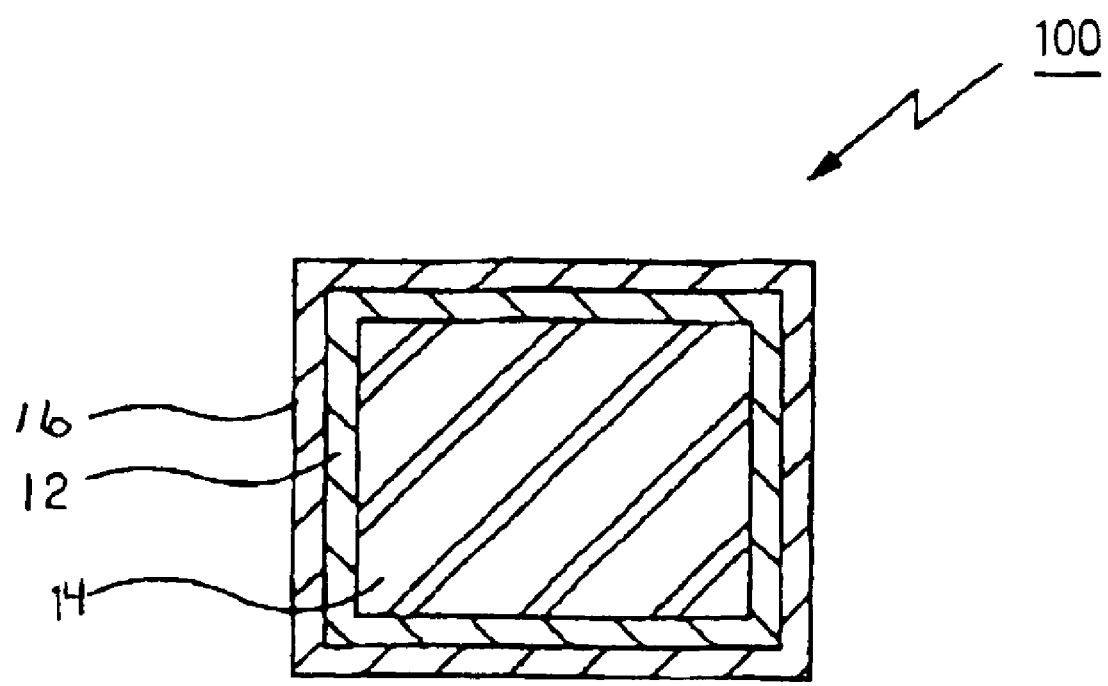
FIG. 6 is a schematic cross section illustrating the material used for the bracelet that radiates anion and far infrared rays.

FIG. 6 is a schematic cross-section illustrating the material used for the bracelet (100) that radiates anion and far infrared rays.

The bracelet (100) in accordance with the present invention is shown in the cross-sectional view of FIG. 6 as including an anion radiating material layer (12) coated on the surface of a metal core (14), and a gold (or silver) plate layer (16) applied over the whole surface of the anion radiating material layer (12). The metal core (14) can be any appropriate metal such as upper, brass, iron, tin or alternatively it may alternatively be a polymeric material.

The anion radiating material layer (12) formed on the surface of the metal core (14) is for generating anion, and comprises a rare-earth metal such Lanthanum, Cerium and their mixtures. In order to enhance the radiation effect of the anion and far infrared rays, it is desirable to use mineral extracted from volcanic ashes.

Rare-earth metals include Scandium, Yttrium, and the Lanthanides series, i.e., the elements with numbers 57 through 71. The Lanthanum Group includes 14 elements starting from Cerium. The six elements from Lanthanum to Samarium are called the Cerium group, those from Europium to Lutetium also belong to the rare earth elements, however, Promethium is a radioisotope, and no stable isotope exists. There are less odd-numbered elements than even-numbered ones, and generally rare-earth metals are silvery-white or gray. Further, these metals oxidize slowly when exposed to air, and melt in acid and hot water, but not in alkali. These metals are very similar chemically, and usually positively trivalent compounds are made, but +4 valent for Cerium, Praseodymium, and positively divalent for Ytterbium, Europium, and Samarium. Similar to alkali metal and alkali earth metal, rare-earth metals have strong positive charge, and their hydroxides are basic.

Figure 7:
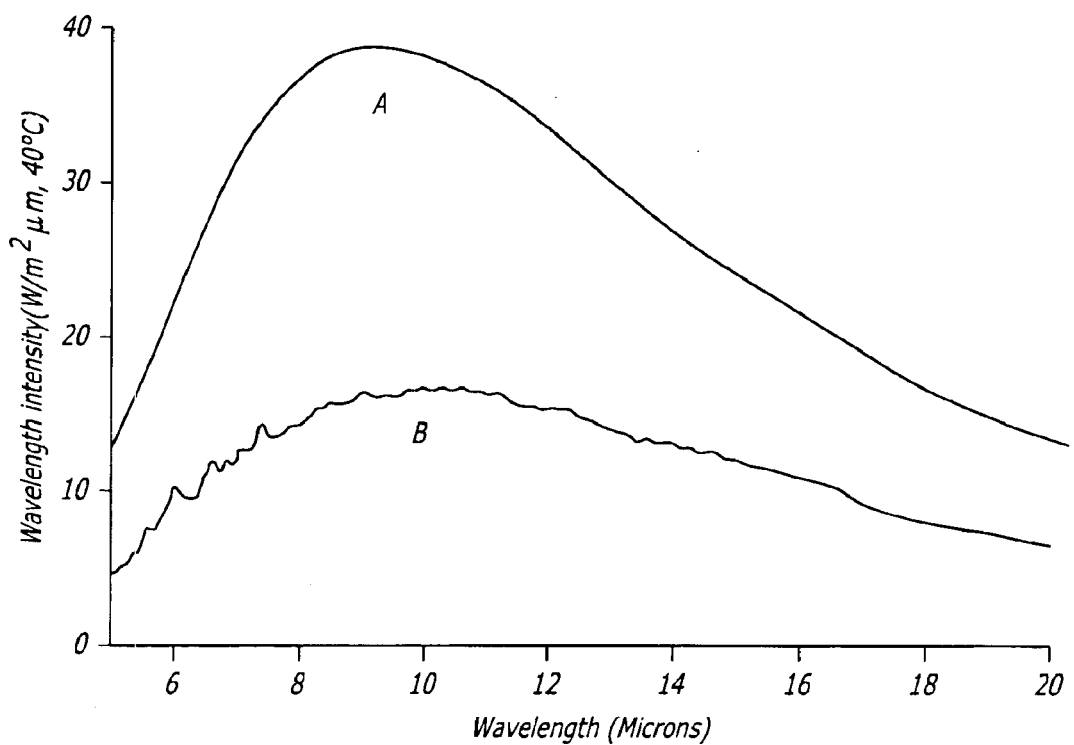
FIG. 7 is a graph illustrating the comparison between radiation strength of a black body (A) and far infrared rays of the bracelet (B) that radiates anion and far infrared rays.

FIG. 7 is a graph illustrating the comparison between radiation strength of black body (A) and far infrared rays of the bracelet (B) that radiates anion and far infrared rays.

The bracelet, in accordance with the present invention, that radiates anion and far infrared rays can be designed by making one axle longer of the connecting arm (20, 21) than the other one, and the same result can be obtained.

In order to understand better the bracelet, in accordance with the present invention the following non-limiting examples are illustrated.

EXAMPLE 1

A molded bracelet, (100), that irradiates anion and far infrared rays was made by using for the core (14) a metal, a ceramic or a polymeric material.

An anion radiating material layer (12) that irradiates significant amounts of anion is formed on the core (14) by coating anion radiating material made of minerals extracted from rare-earth metal, volcanic ashes on the surface of the core (14).

Next, a gold plate layer (16) was formed by coating gold film on the whole surface of the anion radiating material layer (12). In this manner, a metal material was prepared that can be used for making a bracelet that irradiates anion and far infrared rays in accordance with the present invention.

By using the core (14), a C-shape main part (10) was formed, and connecting arm (20) was installed which can rotate where both ends of the main part (10) have pins to act as axles, with one end of the connector (20) combined an end of the main part (10) by the hinge pin (25).

The connecting arm (20) is formed longer than the clasp (21) so that the bracelet (100) in accordance with the present invention that irradiates anion and far infrared rays can be opened/closed more easily.

A clasp (30) is formed at the end of the connector (20) opposite the end connected to the main part (10). The clasp (30 includes a magnet (33) installed so that the clasp (30) can be connected to make clasp 21 which may also include a magnet 33'.

The clasp (30) is composed of part (35) containing the magnet (33) and a fixing part (34) that holds the magnet (33), and a projection (36) installed around the magnet (33) so that the magnet (33) cannot be detached from the clasp (30) because it is firmly stuck to the fixing part (34).

EXAMPLE 2

A test for a necklace made in the same manner that the bracelet was made, in accordance with the Example 1 of the present invention, that irradiates anion and far infrared rays, was requested of the Application & Evaluation Center of Far Infrared Rays, Korea Institute of Construction Materials for measuring the amount of anion irradiation, irradiation strength and emissivity of far infrared rays.

The amount of anion radiated from the bracelet in accordance with the present invention that radiates anion and far infrared rays was measured as follows.

By using the device measuring charged particles, the test was done under the condition of 23/° C., humidity of 58%, and the number of anions in atmosphere was 21/cc. The number of anions irradiated from the article tested was measured and the number was calculated per unit volume, which is as follows:

| Sample Name | Item Anion (ION/cc) |
|---|---|
| Necklace | 23 |

The far infrared rays irradiated from the bracelet in accordance with the Example 1 of the present invention that irradiates anion and far infrared rays was measured compared to Black Body at 40/° C., by using FT-IR Spectrometer, and the result is as follows.

| Emissivity (5~20 μm) | Irradiation Energy (W/m$^2$) |
|---|---|
| 0.437 | $1.76 \times 10^2$ |

As shown in FIG. 7, the energy of $1.76 \times 10^2$ W/m$^2$ irradiated from the bracelet in accordance with the present invention that irradiates anion and far infrared rays, after comparing the irradiation strength of the bracelet at a wavelength between 5 and 20 μm to the Black Body at 40/° C.

Figure 8:
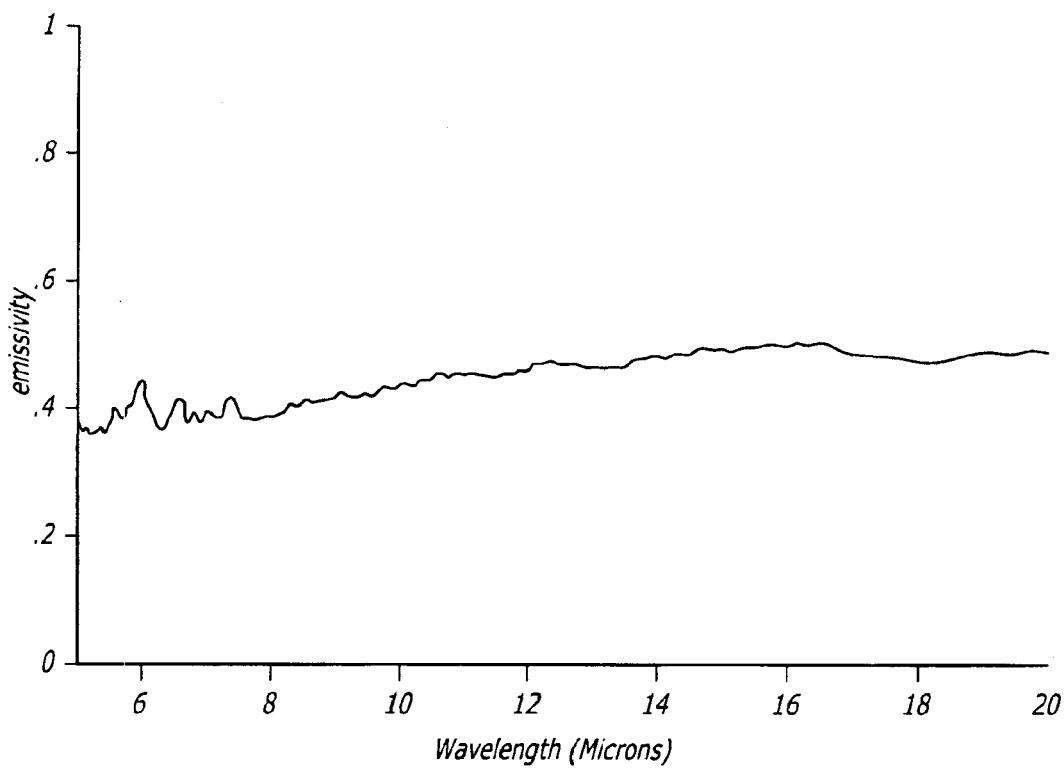
FIG. 8 is a graph illustrating emissivity of the far infrared rays of the bracelet that radiates anion and far infrared rays.

As shown in FIG. 8, the emissivity of the bracelet in accordance with the present invention that irradiates anion and far infrared rays is 0.437, i.e., 44% at a wavelength between 8 and 14 μm, and even at higher wavelength, nearly similar emissivity was maintained.

The bracelet, in accordance with the present invention, that irradiates anion and far infrared rays was allowed to be worn by 50 patients with either the problem of blood circulation such as stitching in the shoulder or whole body or the problem of suffering from neuralgia in the wrist was targeted.

The result was that all the patients wearing the bracelet felt the aches steadily decrease and, after about 15 days, the aches nearly disappeared.

As described above, the bracelet that irradiates anion and far infrared rays, in accordance with the present invention, has an elegant appearance due to its gold plate and can be used as a bracelet as an accessory, and it does not give any inconvenience to the human body since it is attached to the body.

The bracelet in accordance with the present invention can irradiate anion and far infrared rays more effectively through static electricity occurred at the friction between bracelet and skin as well as sunlight, and by regulating cellular ion balance, the electric charge inside and outside the skin gets normal, and controls complex biorhythm such as promoting blood circulation and metabolism, besides activates body cells, lowers blood pressure to increase regenerate tissues, suppressing aging phenomena.

While various embodiments of the invention have been described, it will be apparent to those of ordinary skill in the art that many more embodiments and implementations are possible within the scope of this invention. Accordingly, the invention is not to be restricted except in light of the attached claims and their equivalents.

What is claimed is:

1. A bracelet that irradiates anion and far infrared rays, comprising a core plated with an anion-radiating material layer and a gold plate layer sequentially coated on the surface of the core, the anion-radiating material layer selected from the group consisting of scandium, yttrium, and lanthanides series, the core formed into a "C" shape main part having an end coupled to a connecting arm having an end including a clasp including a magnet to couple to a clasp also having a magnet attached to an opposite end of said "C" shaped main part.

2. A bracelet that irradiates anion and far infrared rays in accordance with claim 1 wherein the clasps have end parts comprising a projection and a mating space containing the magnets.

3. A bracelet that irradiates anion and far infrared rays, the bracelet comprising:
   a metal core having an arc configuration with two free ends;
   an anion-radiating material layer over the metal core, the anion-radiating material layer selected from the group consisting of scandium, yttrium, and lanthanides series;
   a metal plate layer over the anion-radiating material layer;
   means for coupling two free ends of the metal core; and
   a magnet within the means for coupling the two free ends.

4. The bracelet according to claim 3, wherein the lanthanides series includes 14 elements starting from Cerium.

5. The bracelet according to claim 3, wherein the metal plate layer is gold.

6. The bracelet according to claim 3, wherein the metal plate later is silver.

7. The bracelet according to claim 3, wherein the means for coupling is a pair of claps, wherein each of the pair of claps is provided with the magnet.

8. The bracelet according to claim 7, wherein each of the pair of claps has an end part comprising a projection and a mating space containing the respective magnet.

* * * * *